(12) United States Patent
Di Martino et al.

(10) Patent No.: US 11,464,454 B2
(45) Date of Patent: Oct. 11, 2022

(54) DEVICE FOR LEG AND FOOT POSITIONING IN A FOOTPRINT DIGITALIZATION SYSTEM

(71) Applicant: Di Martino snc di Mariano e Giovanni Di Martino, Varese (IT)

(72) Inventors: Mariano Di Martino, Varese (IT); Giovanni Di Martino, Varese (IT)

(73) Assignee: DI MARTINO SRL, Lecco (IT)

( * ) Notice: Subject to any disclaimer, the term of this patent is extended or adjusted under 35 U.S.C. 154(b) by 695 days.

(21) Appl. No.: 16/527,772

(22) Filed: Jul. 31, 2019

(65) Prior Publication Data
US 2020/0069256 A1    Mar. 5, 2020

(30) Foreign Application Priority Data

Aug. 9, 2018 (IT) .................. 102018000007990

(51) Int. Cl.
| | | |
|---|---|---|
| *A61B 5/00* | (2006.01) | |
| *G16H 30/40* | (2018.01) | |
| *A61B 5/103* | (2006.01) | |
| *A61F 5/01* | (2006.01) | |

(52) U.S. Cl.
CPC ............ *A61B 5/702* (2013.01); *A61B 5/1036* (2013.01); *A61F 5/0127* (2013.01); *G16H 30/40* (2018.01)

(58) Field of Classification Search
CPC ..... A61F 5/0127; A61B 5/1036; A61B 5/702; G16H 30/40
See application file for complete search history.

(56) References Cited

U.S. PATENT DOCUMENTS

| | | | | |
|---|---|---|---|---|
| 4,662,079 A | * | 5/1987 | Graf | ........................ A43B 7/28 33/3 R |
| 7,975,390 B2 | * | 7/2011 | Goonetilleke | ........... A43D 1/02 33/515 |
| 9,615,814 B2 | * | 4/2017 | Luo | ...................... A61B 8/0875 |
| 2012/0053490 A1 | | 3/2012 | Smith | |

FOREIGN PATENT DOCUMENTS

| | | |
|---|---|---|
| EP | 2186429 | 5/2010 |
| WO | WO 2016093955 | 6/2016 |
| WO | WO 2017125896 | 7/2017 |

OTHER PUBLICATIONS

EPO Search report, application 19020460.2-1011.

\* cited by examiner

*Primary Examiner* — Gregory H Curran
(74) *Attorney, Agent, or Firm* — Neifeld IP Law PLLC (57) ABSTRACT

The present invention relates to an apparatus comprising: a seat for a patient; a support platform for the feet of the patient, positioned anteriorly to the seat; an alignment system allowing a patient's leg and its corresponding foot to be aligned in the three space planes in order to determine the tibia correct verticality; a system for properly positioning the foot on the platform including at least turrets able to allow pads to be applied in contact with the talus and/or scaphoid inside the foot and in contact with the calcaneus and/or cuboid outside the foot; a foot measurement system in a neutral position; an automatic real time driving system for properly positioning the leg and foot with numerical indication and direction of the movements to be carried out; a central unit capable for receiving and processing the data detected by the measurement system for footprint digitalization.

10 Claims, 7 Drawing Sheets

DEVICE FOR LEG AND FOOT POSITIONING IN A FOOTPRINT DIGITALIZATION SYSTEM

CROSS REFERENCE TO RELATED APPLICATIONS

This application claims priority benefit to Italian application No. 102018000007990, filed Aug. 9, 2018. The content and claims of these preceding applications are hereby incorporated by reference in their entirety.

FIELD OF INVENTION

The present invention relates to a system for footprint digitalization for the orthotics construction; in particular, the present invention relates to a device for the correct leg and foot positioning in a system for digitizing the relative footprints.

STATE OF ART

Footprint digitization systems so far known have many drawbacks, since they do not allow and do not provide for a spatial leg and foot alignment in optimal conditions, they do not include a measurement system for detecting the limb and foot position, and therefore do not allow a numerical instrumental evaluation of the leg and foot position; they also do not allow the foot to be held in a neutral condition.

In fact, at present the state of the art provides systems for detecting the footsole shape, both manual and digital, wherein the patient is placed in an alignment visually assessed by the operator, with the sole help of a reference visual system, but without any instrumental verification and numerical measurement of the actual leg and foot position when detecting the footsole shape. Most operators manually perform this operation by raising the patient standing on phenolic foam to detect the pattern footprint.

For example, the US patent application published with n. US 2012/053490 A1 describes an apparatus for detecting foot prints, wherein the forefoot positioning, in particolar the 5 metatarsal positioning, is used. This positioning acts as a support for the foot and no thrusts or movements occur in order to establish a correct foot and leg alignment in a neutral position.

An obvious limitation of these alignment systems is the operation non-repeatability as it is entrusted exclusively to the visual operator verification; in such systems known in the art there is therefore the impossibility of being able to physically obtain for all patients a footprint having exactly the same leg and foot positioning characteristics at the time of acquisition of the footsole or footprint shape. This footprint is the basis for the subsequent orthoses (or orthotics) construction tailored to the patient. This drawback, namely the lack of a certain operation repeatability and therefore the lack of standardization of leg and foot positioning when the footprint is taken, determines the impossibility of preparing a production system that guarantees the same index of functionality for all orthoses and orthotics produced.

Therefore, currently the state of the art does not allow, in the control of effectiveness and functionality and subsequent modification of the orthoses and orthotics produced, an instrumental and numerical verification of the leg and foot actual position.

A further problem is determined by the fact that the footprint is detected in an incorrect and pathological condition. With this methodology we obtain a model that does not allow us to trace the neutral and functional foot position, which is fundamental for the perfect orthesis realization.

Therefore, the Applicant of the present patent application has found the need to provide a device for positioning the leg and the foot in a footprint digitalisation system which solves the aforementioned technical problems present in the known in the art systems.

SUMMARY OF THE INVENTION

In a first aspect, the present invention relates to an apparatus for the automated footprints detection of a patient such as that one indicated in claim 1.

The Applicant of the present application has in fact surprisingly found that the above technical problem can be effectively and reliably solved by means of an apparatus for the automated footprint detection of a patient in a seated or standing position, whether the patient is wearing or not an orthotic. The apparatus of the present invention comprises:
- a seating position, adjustable in height, for said patient when he/she is in a sitting position;
- a support platform for the feet of said patient, provided with at least two degrees of freedom, and which is positioned at front of said seating position, at a lower level with respect to it;
- an alignment system allowing a patient's leg and its corresponding foot to be aligned in the three space planes in order to determine the correct tibia verticality, wherein said alignment system comprises at least two markers, in which at least one first marker is placed at the knee, frontally at the midpoint of the segment joining the lateral and medial femoral condyle, and at least one second marker is placed at the space between the second and third metatarsal;
- a system for the correct foot positioning on said support platform which includes at least two micrometric adjustment devices, also known as turrets, placed laterally with respect to the foot and capable of sliding on a track along a platform direction, wherein at least one of said turrets is able to allow at least a first adjustable pressure pad to be applied into contact with the talus and the scaphoid inside the foot and at least another of said turrets is able to allow at least one second adjustable pressure pad to be applied into contact with the calcaneus and/or cuboid outside the foot;
- a continuous measurement system able to numerically detect the data relating to said leg and foot alignment in the three space planes;
- a central unit capable of receiving said data detected by said continuous numerical measurement system and capable of possibly providing the numerical and directional directions of movement necessary for the correct leg and foot repositioning to obtain the desired leg and foot vertical alignment for the subsequent footprint digitization.

In this way, the apparatus of the present invention allows to perform the operations for taking a footprint with a seated patient and with the leg and the foot aligned in the three space planes.

The apparatus also allows to compare the foot rest with respect to the overlying bones position up to the knee joint and to cross these biometric references to improve the foot care study.

With this apparatus the footprints can always be detected under the same conditions, ensuring the measurement repeatability, and with the foot in a neutral position, or in the position in which it should be if it is in not pathological condition. This computer-assisted operation makes it possible to measure the leg and foot bones position in real time and provides the information necessary to automatically bring the limb into alignment in the precise coordinates required for the correct taking of measurements.

When checking a therapy or checking the orthoses effectiveness, the doctor or technician will be able to have the data on the over-segmental angular rotations and at the same time check the plantar support by having a forensic medical report.

Conversely, in the state of the art, medical evaluation is simply objective (clinical examination).

With this apparatus, the tecnica sector is provided with a measuring instrument useful for diagnostic, productive and forensic medical purposes.

According to a preferred embodiment of the present invention, said patient's leg alignment system with its corresponding foot comprises a plurality of reflective markers placed at reference points.

In this way, the markers allow to evaluate the tibia verticality, which can occur by analyzing the relative displacements between the limb joints, such as ankle and knee.

According to a preferred embodiment of the present invention, there are at least five of said markers positioned respectively at the inner knee or medial tibial condyle, external knee or lateral tibial condyle, internal malleolus, external malleolus, and foot dorsum or space between the second and third metatarsal. In this way, the tibia is modeled as the segment having for its extremes the midpoints of the junctions the lower and upper pairs of markers.

The presence of these five markers allows a first type of position detection in normal conditions, with the patient in a sitting position, and with the leg and foot alignment in a neutral position. This first type of detection is used for repositioning the patient's leg and foot in a neutral position necessary for detecting the footsole shape according to the following steps: a) vertical alignment in the frontal and lateral plane of the line originating at the midpoint of the segment between the lateral tibial condyle and the medial tibial condyle and passing in the midpoint of the segment between the lateral malleolus and the medial malleolus, and b) after this alignment, repositioning in the condition of foot neutral position by manipulating the meso-foot, by exerting a force in external rotation on the scaphoid and/or astragal and cuboid bones through a special lever until the condition of foot neutral position occurs.

The presence of these five markers also allows a second type of position detection in normal conditions and with orthosis, with the patient standing. Furthermore, measurement of bone segments between markers is also allowed; the verification of the differences in the leg and foot position between the pathological condition without the use of the plantar and the leg and foot position with the use of the plantar; verification of changes in leg and foot position when changing the orthosis; verification of changes in the leg and foot position following tests carried out directly on the orthosis before the modification of the same, and the subsequent oerthosis verification after the modification.

Furthermore, the measurements of the bone segments performed with the function of detecting the position with five markers with the patient in an upright position on both legs also allows the numerical evaluation of any existing morphological differences between the two legs, as well as the differences in position between the two legs with and without orthotics.

According to a preferred embodiment of the present invention, said alignment system of a patient's leg with its corresponding foot comprises at least seven of said markers, positioned respectively at the lateral tibial condyle (or outer knee), medial tibial condyle (or inner knee), lateral malleolus, medial malleolus, cuboid bone, astragalus or scaphoid bone salience, foot dorsum or space between the second and third metatarsal.

In this way, thanks to the presence of two further markers with respect to the embodiment with at least five markers described above, in particular the markers placed at the cuboid bone and at a salience of the talus or scaphoid bone, it is possible to obtain more precise information relative to the tibia and foot alignment.

This platform on which the foot rests has two degrees of freedom, and is therefore able to move parallel and perpendicular to the seat axis.

According to a preferred embodiment of the present invention, the upper plane of said platform is able to be automatically adjusted so as to be brought into the condition of said tibia verticality, or in the condition in which the line which originates in the midpoint of the segment between the lateral tibial condyle and the medial tibial condyle and which passes at the midpoint of the segment between the lateral malleolus and the medial malleolus is vertically aligned in the frontal and lateral plane.

In a first embodiment, the platform is manually adjusted. In this manual mode, the verticality is measured on the tibia lateral and frontal planes so as to provide indications of the movement direction (left, right, forward, back) of the plane to reach said verticality condition and information on distance (in millimeters and tenths) of movement of the plane on which the foot rests to bring the tibia in a vertical position on the frontal and lateral plane.

In a second embodiment, said platform adjustment automatically takes place: the bone position of the leg and of the foot are analyzed through the markers in real time by the central unit, such as a computer, on the basis of the collected data, the central unit imparts the movements necessary to automatically bring the platform plane into the precise coordinates requested by means of an electronic motor automatically guided by said central unit, for the correct measurements taking, and therefore the limb in vertical alignment based on the described conditions.

In this way, the problems of limb positioning on the X-Y-Z orthogonal planes are solved, ensuring the measurement repeatability always in the same conditions.

According to a preferred embodiment of the present invention, said micrometric adjustment devices (turrets) are placed on the support plane of said platform.

According to a preferred embodiment of the present invention, at least one of said micrometric adjustment devices (turret) is arranged medially in correspondence with one foot side and at least another of said micrometric adjustment devices is placed laterally at the opposite foot side.

In this way, the turrets allow the pad application on the foot bony prominences and, through pressure on the foot joint, its correct positioning.

Moreover, in this way, it is not necessary to place any turret or pad in the area below the foot sole.

According to a preferred embodiment of the present invention, said micrometric adjustment devices are provided with at least two degrees of freedom, preferably at least three degrees of freedom, still more preferably five degrees of freedom, in order to allow the best possible adjustment based on the different feet morphology, wherein said micrometric adjustment devices are chosen from: a) lateral sliding to adapt to the foot length, b) height adjustment, c) lateral depth adjustment, d) lateral rotation adjustment with respect to the foot, and e) lever with pad for support on scaphoid/astragalus.

According to a preferred embodiment of the present invention, said lever provides a thrust on the scaphoid and/or astragal bone components so as to bring the mesopod in external rotation until it reaches the position in the condition of neutral position necessary for taking the footprint.

According to a preferred embodiment of the present invention, in the foot medial part said micrometric adjustment device is provided with the five degrees of freedom indicated above.

According to a preferred embodiment of the present invention, in the lateral foot part said micrometric adjustment device is provided with at least three of said five above-mentioned degrees of freedom, such as for example lateral sliding to adapt to the foot length, height adjustment, and lateral depth adjustment.

According to a preferred embodiment of the present invention, said turrets allow an adjustable pressure pad to be applied into foot contact, in particular: a) medially on the scaphoid or/and astragalus, so as to constrain the foot internally, to manipulate the scaphoid or/and astragalus and bring the foot to the correct position indicated by the visual alignment system, and b) laterally on the cuboid and/or calcaneus, so as to provide a block and a counter-thrust to avoid lateral translation.

According to a preferred embodiment of the present invention, said apparatus further comprises a stereo-visual system consisting of a plurality of television cameras, preferably at least two, more preferably at least three, placed frontally with respect to said seating position, able to identify the position of said reflective markers.

In this way, the cameras are able to detect the presence and positioning of the various markers and thus allow the technician or doctor to verify the correct tibia verticality before proceeding with the foot repositioning by manipulating the meso-foot and subsequently to the measurement operations for the footprint realization.

Furthermore, the leg and foot position detection is performed with measurement of the position in space with metric system expressed in tenths of mm or other metric systems with a tolerance of 0.05 mm.

According to a preferred embodiment of the present invention, said central unit is able to analyze in real time the data relating to said leg and foot alignment in the three space planes, and is able to automatically provide the indications of the necessary displacements to automatically bring the platform into the precise coordinates required to obtain the correct the leg and foot repositioning and vertical alignment before proceeding to repositioning the foot by manipulating the meso-foot for the subsequent footprint digitization.

According to a preferred embodiment of the present invention, said foot support platform is constituted by a transparent portion, for example made of glass, to allow a laser scanning device located below said support platform and to the same height of the floor to detect the foot positioning in a neutral position on said platform and to digitize the relative footprint. Said laser scanning device, integrated in said platform, is electronically powered and controlled by said central unit.

In this way, thanks to the platform transparency onto which the foot rests, it is possible to scan the foot for the purpose of making the footprint.

According to a preferred embodiment of the present invention, said laser scanning device is able to transmit to said central unit the detected data relating to the foot measurements in a neutral position on said support platform, in order to be able to carry out the footprint digitization.

In this way the central unit is able to receive, process and store the data to make the footprint and then to eventually compare them in the future with other data obtained during a new control measurement.

In a second aspect, the present invention refers to a method for making a footprint as indicated in claim 10.

The Applicant of the present application has in fact surprisingly found that the technical problem identified above can be effectively and reliably solved by means of a method for digitizing the footprint of a patient's foot comprising the steps of:
a) placing the patient in a sitting position;
b) allowing the patient to rest his/her foot on a support platform;
c) detecting the patient leg and foot correct alignment so that the tibia is in a vertical position using at least one marker placed in front of the knee at the midpoint of the segment that joins the lateral and medial femoral condyle and at least one other marker placed at the space between the second and third metatarsal;
d) positioning the foot in a neutral position by exerting a rotating force on the scaphoid and/or cuboid bones, by means of a lever and at least two micrometric adjustment devices, also known as turrets, placed laterally with respect to the foot and able to slide along a long track a platform direction, wherein at least one of said turrets is able to allow at least one first adjustable pressure pad to be applied into contact with the talus and/or the scaphoid inside the foot and at least one other of said turrets is able to allow at least one second adjustable pressure pad to be applied into contact with the heel and/or cuboid outside the foot, without placing anything under the foot sole;
e) carrying out the continuous numerical data measurement relating to said leg and foot alignment in the three space planes in a neutral position by means of a stereo-visual system consisting of a plurality of cameras able to detect the position of said markers;
f) transmitting to a central unit the measured data of said continuous numerical measurement for processing and storing said data to obtain the footprint digitization;
g) allowing said central unit to possibly provide the indications to correctly reposition the foot in order to obtain the desired leg and foot vertical alignment.

In this way the footprint digitization takes place with the patient in a sitting position, and only after the correct leg and foot alignment has been verified at first and the foot has been placed in a neutral position.

With the method of the present invention the problems reported above are thus solved with reference to the measurement methods known in the art.

According to a preferred embodiment, the method of the present invention first comprises the step of vertically aligning in the frontal and lateral plane the line originating at the midpoint of the segment between the lateral tibial condyle and the medial tibial condyle and passing at the midpoint of the segment between the lateral malleolus and the medial malleolus and, subsequently, the phase of repositioning in a condition of the foot neutral position by manipulating the meso-foot by exerting a force in external rotation on the scaphoid and/or astragal and cuboid bones through a lever up when this line ends and joins vertically in the frontal plane in the space between the second and third metatarsal radius.

According to a preferred embodiment, said central unit automatically controls said leg and foot alignment in said condition of neutral position, providing in real time the numerical and direction parameters expressed in mm or other measurement system relating to the leg and foot joints position.

In this way the numerical parameters relating to the displacement measure necessary to bring the foot to a neutral position and to the repositioning ratios necessary to achieve the alignment of the following joints are calculated in real time: ankle-forefoot, ankle-knee, knee-avampiede.

According to a preferred embodiment, said repositioning is automatically guided by the central unit which, by means of directional arrows, indicates: a) the displacement direction to be made in the right/left direction (lateral-medial), and b) the quantity of such displacements expressed numerically in mm (or in another metric system).

According to a preferred embodiment, when the repositioning for the correct alignment is reached, the central unit emits a light signal, such as a green light, indicating that the foot is at that point in a constrained position such that it is possible to proceed to the next digitization step.

Therefore, the method of the present invention allows to detect the footprints always in the same leg and foot positioning conditions, with the foot in a neutral position, therefore in the position in which it should be if it is in not pathological condition.

Moreover, this operation assisted by the central unit, with the measurements data detected in real time, allows a precision and repeatability with high reliability, useful for diagnostic, productive, medical forensic purposes.

In addition to the foot rest under different instrumentally controlled conditions, it is also possible to compare the foot rest with respect to the overlying bones position, up to the knee joint, and to cross these biometric references to improve the foot care study.

When checking a therapy or checking the orthoses effectiveness, the doctor or technician will be able to have the data on the over-segmental angular rotations and at the same time to check the plantar support by having a forensic medical report.

Further characteristics and advantages of the present invention will be better highlighted by examining the following detailed description of a preferred but not exclusive embodiment, illustrated by way of non-limiting example, with the aid of the attached drawings, in which.

DETAILED DESCRIPTION

The following detailed description refers to a particular embodiment of the system of the present invention, without limiting its content.

Figure 1:
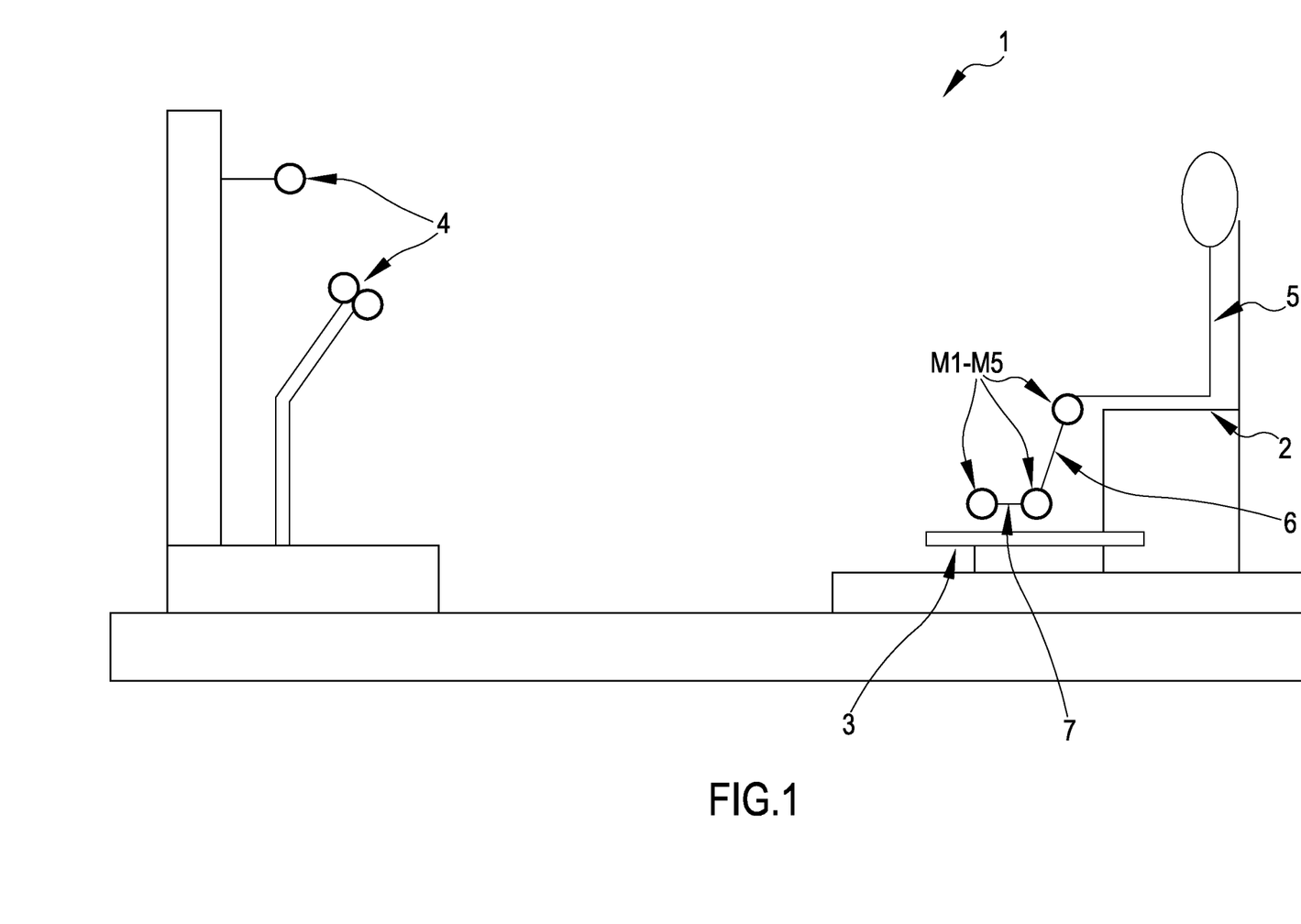
FIG. 1 is a schematic side section view of an embodiment of the apparatus of the present invention.

With particular reference to FIG. 1, an apparatus 1 for making the footprints of the foot 7 of a patient 5 is described. The apparatus 1 comprises a height-adjustable seat 2 onto which the patient 5 sits; in front of the seating position 5, a platform 3 for supporting the feet 7 of the patient 5, at a lower level with respect to it, is placed. The platform 3 is provided with two degrees of freedom, longitudinal and transverse.

The apparatus 1 also comprises an alignment system consisting of a series of markers M1-M5 (better visible in FIG. 2) and a stereo-visual system 4.

The markers M are positioned, respectively, in correspondence of the inner knee or medial tibial condyle (M1), external knee or lateral tibial condyle (M2 marker), internal malleolus (M3 marker), external malleolus (marker M4) and foot dorsum or space between the second and third metatarsal (marker M5). In FIG. 1, being a side view, only three markers are visible, since the markers M1 and M2, respectively positioned at the inner knee and the outer knee, are aligned and so only one of these markers M1 and M2 is visible. Similarly, the markers M3 and M4, respectively positioned at the internal malleolus and the external malleolus, are also aligned and therefore only one of these markers M3 and M4 is visible.

The stereo-visual system 4 consists of three cameras placed frontally with respect to seat 2 and able to detect the placement of the markers M1-M5.

This alignment system, consisting of the markers M1-M5 and the cameras 4, allows to align in the three space planes a leg 6 of the patient 5 (shown in FIG. 2) and its corresponding foot 7 so as to determine the correct tibia verticality, analyzing the relative displacements between the joints of the limb, such as ankle and knee. The tibia verticality is reached when, in the frontal plane, the line 9 (FIG. 2), originating from the center of the knee and ends in the space between the second and third metatarsal radius, and passing at the midpoint located between the tibial condyle lateral and the medial tibial condyle, and between the lateral malleolus and the medial malleolus, is vertically aligned.

This operation is automatically controlled through a central interface unit that evaluates the position in real time until alignment in neutral position is reached. Once this alignment is reached, foot 7 is constrained to proceed to the next digitization phase.

Figure 2:
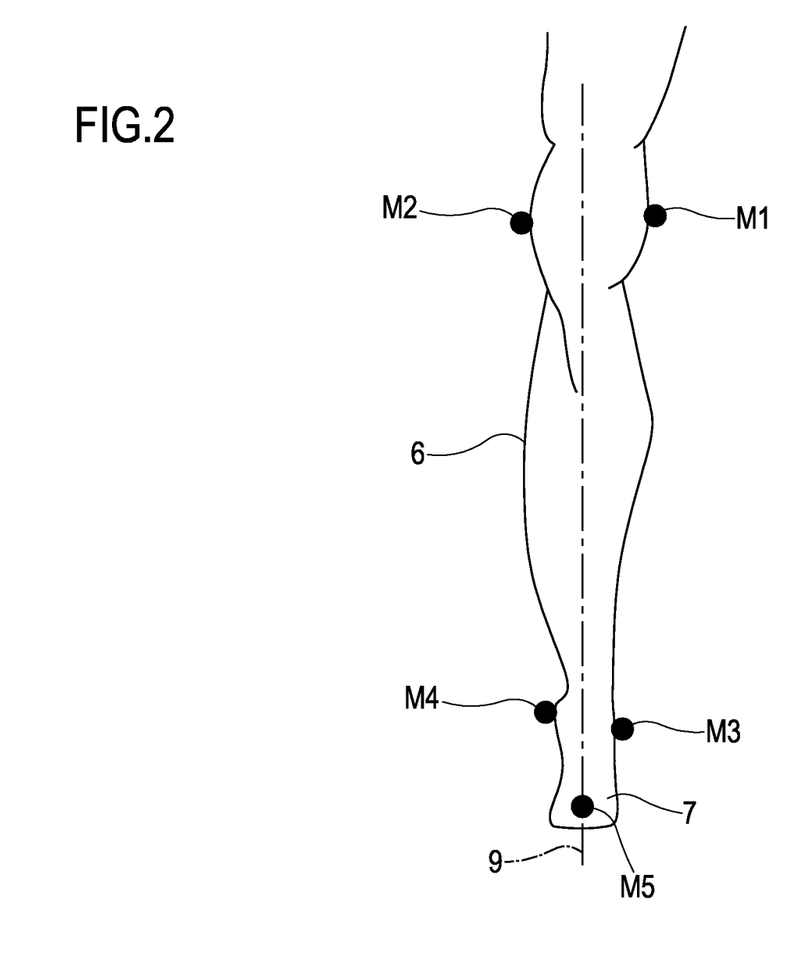
FIG. 2 is a front view of a patient leg to which five markers have been applied according to an embodiment of the present invention.

Only after this alignment, the foot 7 repositioning in a neutral position occurs by manipulating the meso-foot by exerting a force in external rotation on the scaphoid and/or astragal and cuboid bones by means of the lever 10 until this line 9 ends and vertically joins in the frontal plane in the space between the second and third metatarsal radius.

Figure 3:
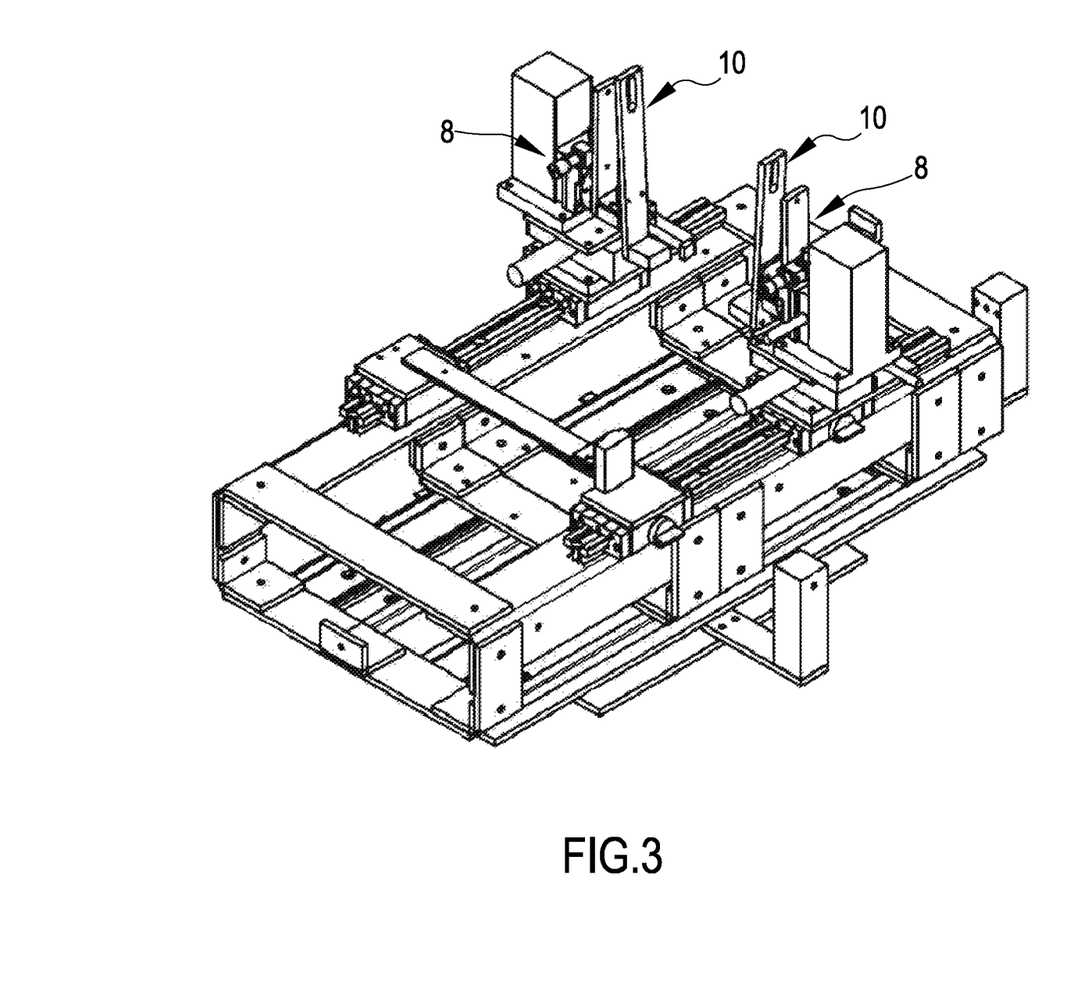
FIG. 3 is an axonometric view of a detail of the apparatus of FIG. 1 wherein two turrets are visible.
Figure 4A:
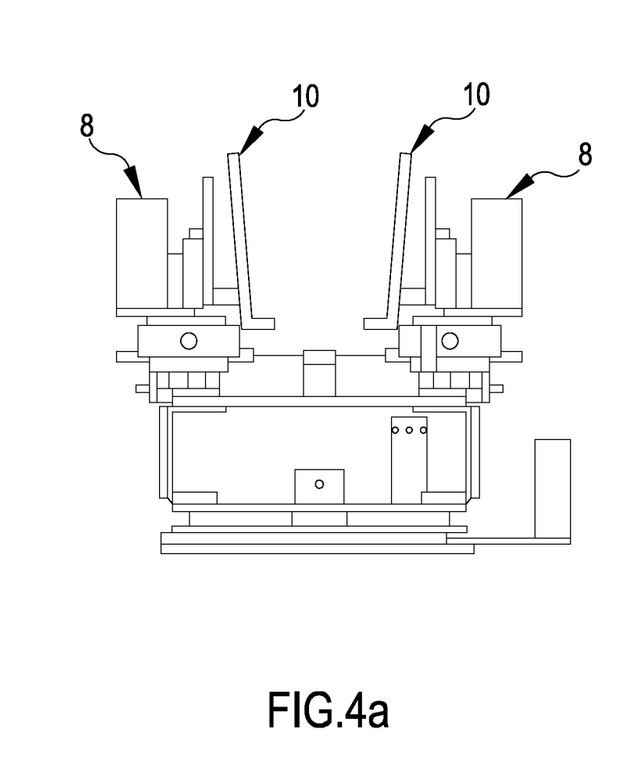
FIGS. 4a and 4b are respectively a front and a side view of the detail of the apparatus of FIG. 3.
Figure 4B:
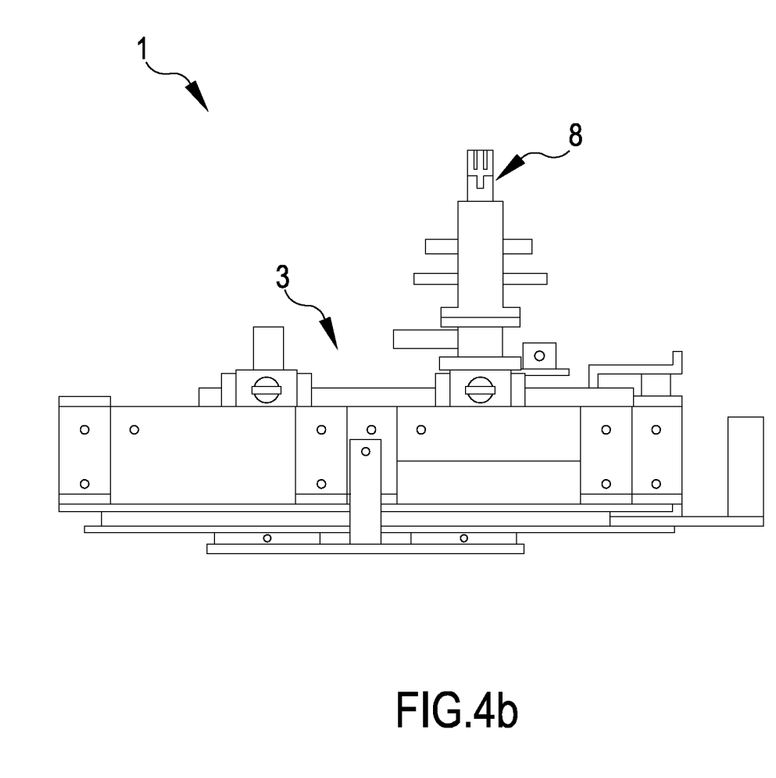
Figure 5A:
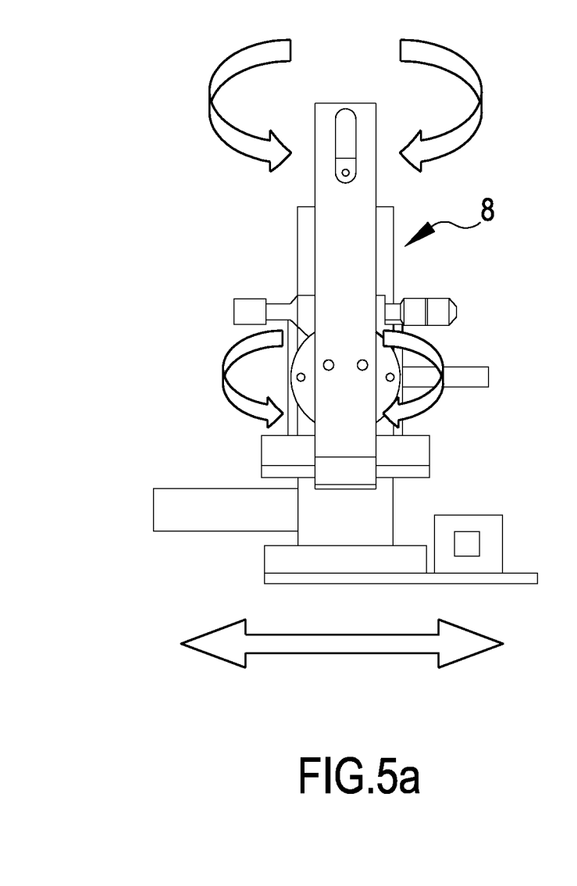
FIGS. 5a and 5b are schematic side views showing the degrees of freedom of the turret of FIGS. 3, 4a and 4b.
Figure 5B:
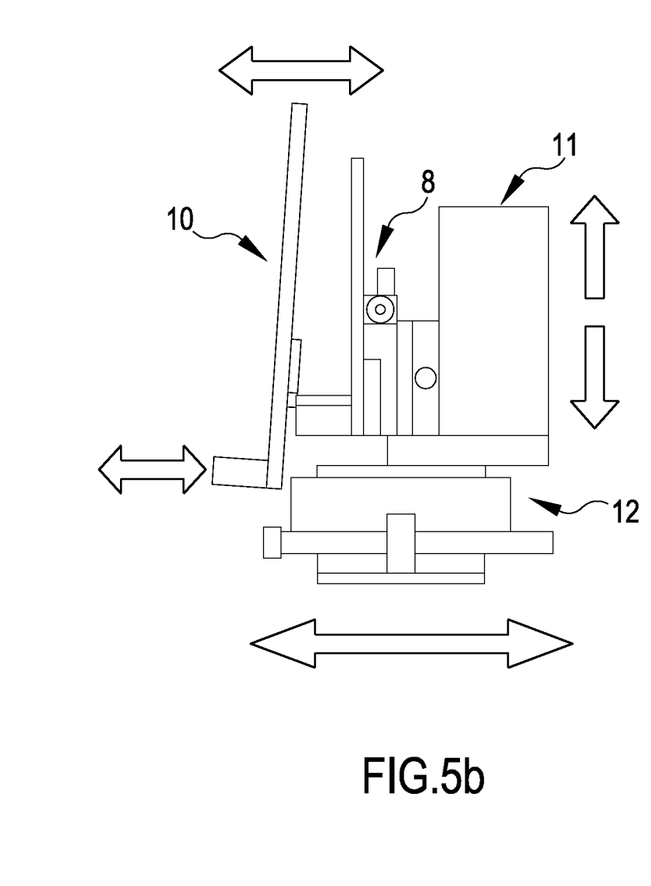

To this end, the apparatus 1 further comprises two turrets 8 (FIGS. 3 and 4), positioned on the support platform 3, so that a turret 8 is in correspondence with one foot 7 side and the other turret 8 in correspondence of the opposite foot 7 side. Each of the turrets 8 is able to slide on a rail along a platform 3 direction, and allows at least one adjustable pressure pad to be applied into contact with the foot 7. The degrees of freedom of the turrets 8 are shown in FIG. 5, where the block 11 allowing the height adjustment of the point of application of the force and the block 12 allowing to approach/move away from the foot are also visible.

From the operational point of view: a first pad is medially applied in the area of the talus and/or scaphoid inside the foot 7; a second pad is laterally applied in contact with the calcaneus and/or cuboid outside the foot 7, so as to provide a block and a thrust to avoid lateral translation. After correctly positioning and orienting the pads on the bony prominences of the foot 7, the necessary pressure is exerted on the foot 7 using the lever 10 (FIG. 5) so that the midfoot joint is correctly positioned. The lever 10 allows to adjust both the force modulus and the force inclination with respect to the horizontal plane of the platform 3 onto which the scanner is positioned.

The support platform 3 is constituted by a portion of transparent material, such as glass. This allows a laser scanning device (not shown in the figure), arranged at the support platform 3, to detect the foot 7 positioning in a neutral position and to carry out the relative continuous numerical measurements for processing and storing data to get the footprint digitized.

Moreover, this laser scanning device is able to transmit to the central unit the data collected relating to the measurements of the foot 7 in a neutral position, in order to be able to carry out the footprint digitization.

Figure 6:
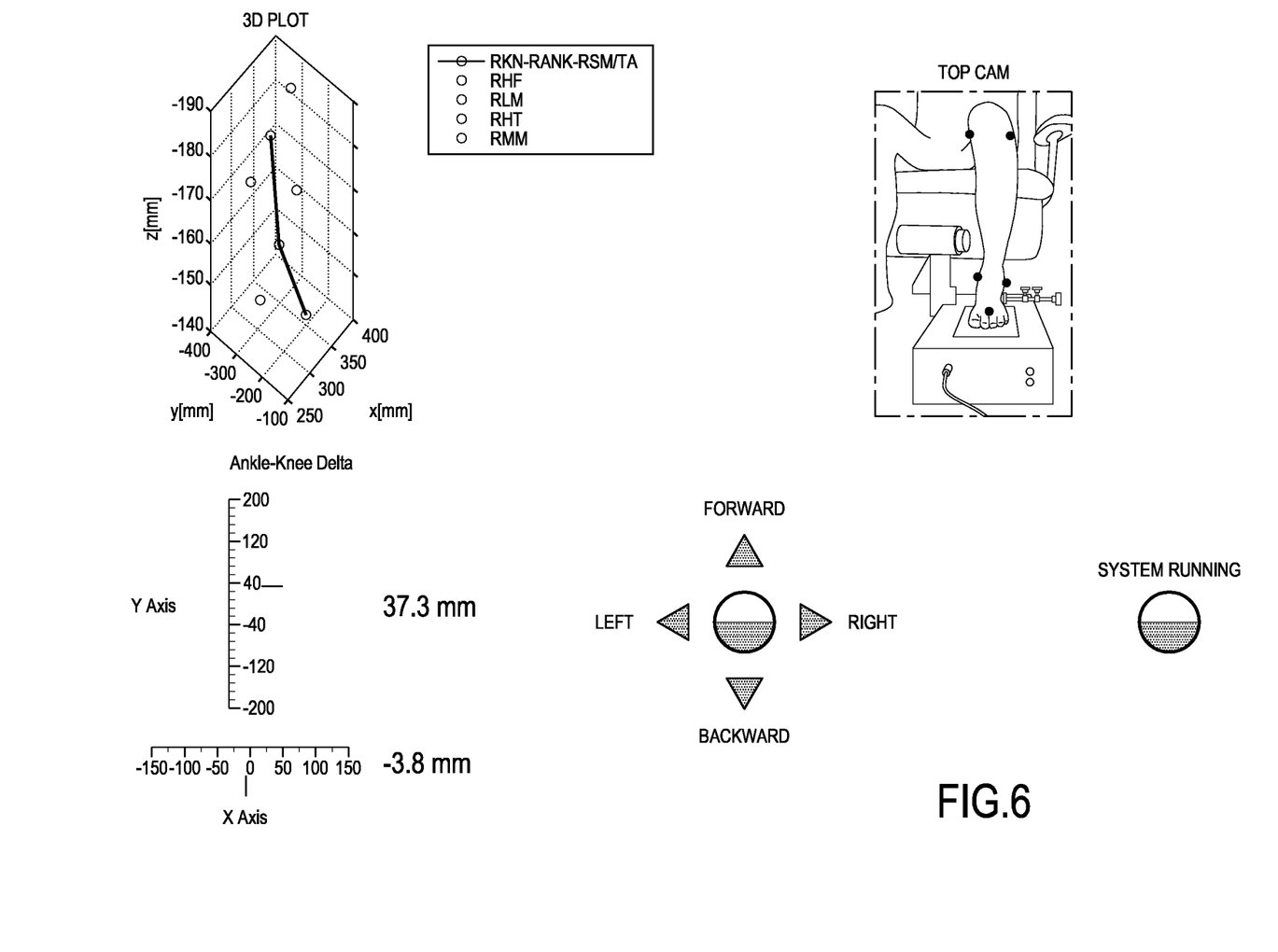
FIG. 6 shows a screen of a leg vertical alignment phase according to the method of the present invention.
Figure 7:
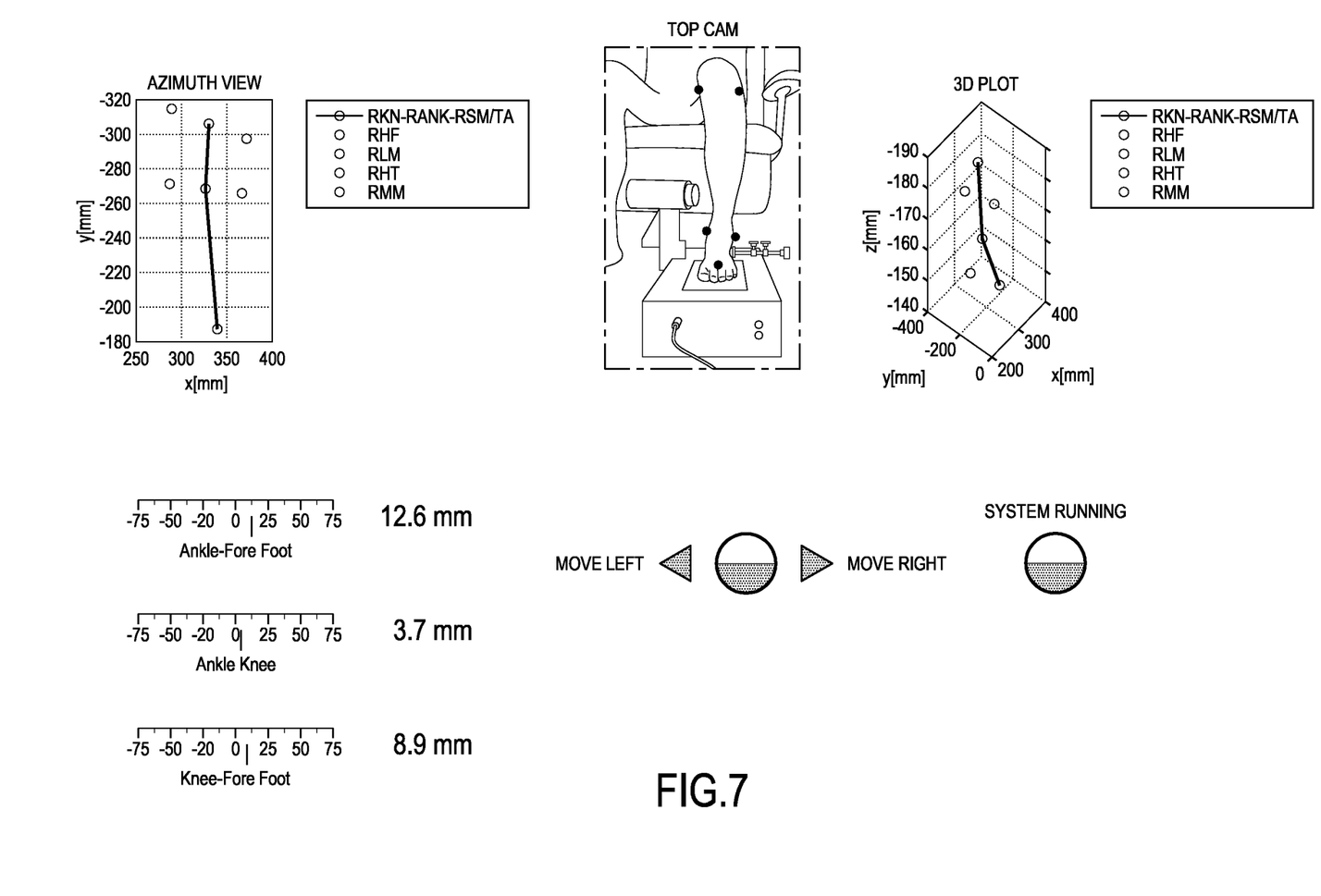
FIG. 7 shows a screen of an alignment repositioning step in the condition of foot neutral position according to the method of the present invention.

FIGS. 6 and 7 show two screens visible on a display the apparatus 1 of the present invention is provided of, in which are reported the numerical and graphical data relating, respectively, to the leg 6 vertical alignment and to the by alignment foot 7 repositioning in condition of neutral position in a specific measurement case.

In particular, FIG. 6 shows a three-dimensional graph relating to the leg alignment, the measured numerical data relating to the ankle-knee joint ("ankle-knee") along the Y axis (37.3 mm) and long the X-axis (−3.8 mm). Arrows of lighter color are also reproduced which indicate that a shift to the left ("left") and back ("backward") is necessary to obtain a correct positioning.

Vice versa, FIG. 7 shows a three-dimensional graph relating to the foot repositioning for the neutral position, as well as the measured numerical data relating to the ankle-forefoot joint ("ankle-forefoot") of 12.6 mm, to the joint ankle-knee ("ankle-knee") of 3.7 mm, and to the knee-forefoot joint ("knee-forefoot") of 8.9 mm.

Arrows of lighter color are also reproduced indicating that a shift to the right ("move right") is necessary to obtain a correct repositioning.

In this way, the apparatus of the present invention allows to perform the operations for taking the footprint of a seated patient 5 and with the leg 6 and the foot 7 aligned in the three space planes.

In the embodiment described above with reference to FIGS. 6 and 7, the screen is positioned in front of the patient with the operator beside the patient; therefore the references indicated above as "to the left", "to the right", "forward", "back" are to be understood with reference to the operator's point of view in that specific position.

With this apparatus the footprints can always be detected under the same conditions, ensuring the measurement repeatability, and with the foot 7 in the condition of neutral position, or in the position in which it should be if it were not in pathological condition. In this way the footprint digitization takes place with the patient 5 in a sitting position, and only after the correct leg 6 and foot 7 alignment has been first verified and that, subsequently, the foot 7 has been placed in position neutral.

This computer-assisted operation allows the numerical parameters measuring expressed in mm or in other measurement systems related to the position of the joints and bones of leg 6 and foot 7 in real time. In this way the numerical parameters relating to the displacement measure necessary to bring the foot to a neutral position and to the repositioning ratios necessary to reach the alignment of the ankle-forefoot, ankle-knee, knee-forefoot joints are calculated in real time.

The foot repositioning in a neutral position is automatically guided by the central unit which, using directional arrows (see FIG. 7) indicates the movement direction to be made in the right/left direction (lateral-medial), and the number of such movements expressed numerically in mm (or in another metric system).

When repositioning is achieved for proper alignment, the central unit emits a light signal, such as a green light, indicating the foot is at a constrained position so that it is possible to proceed to the next digitization step.

With the method of the present invention the above reported problems are thus solved with reference to the known in the art measurement methods.

In fact, the method of the present invention makes it possible to detect the footprints always in the same conditions of leg and foot positioning, with the foot in a position of neutral position, therefore in the position in which it should be if it were in not pathological condition.

Moreover, this operation assisted by the central unit, with the measurements data detected in real time, allows a high reliability precision and repeatability, useful for diagnostic, productive, medical forensic purposes.

Of course, many modifications and variations of the described preferred embodiments will be apparent to those skilled in the art, still remaining within the scope of the invention.

Therefore, the present invention is not limited to the describe preferred embodiments, illustrated only by way of example and not for limiting purposes, but is defined by the following claims.

The invention claimed is:

1. Apparatus (1) for automated footprints (7) detection of a patient (5) in a seated or standing position, and/or when the patient is wearing or not an orthotic, including:
   a seating position (2), adjustable in height for said patient (5);
   a platform (3) for supporting feet (7) of said patient (5), provided with at least two degrees of freedom, and which is positioned at the front of said seating position (2), at a lower level with respect to the seating position;
   an alignment system allowing a patient (5) leg (6) and its corresponding foot (7) to be aligned in the three space planes in order to determine a correct tibia verticality, wherein said alignment system comprises at least two markers (M), wherein at least one first marker is placed at the knee, frontally at a midpoint of a segment joining the lateral and medial femoral condyle, and at least one second marker is placed at a space between the second and the third metatarsal;
   a system for properly positioning the foot (7) on said supporting platform (3) which includes at least two micrometric adjustment devices (8), also known as turrets (8), placed laterally with respect to the foot (7) and able to slide on a track along a platform (3) direction, wherein at least one of said turrets (8) is able to allow at least one first adjustable pressure pad to be applied in contact with the talus and/or scaphoid inside the foot (7) and at least another one of said turrets (8) is able to allow at least one second adjustable pressure pad to be applied in contact with the calcaneus and/or cuboid outside the foot (7);
   a continuous measurement system able to numerically detect a data relating to said leg (6) and foot (7) alignment in the three space planes;
   a central unit capable of receiving said data detected by said continuous numerical measurement system and capable of possibly providing the numerical indications and movement direction necessary for a correct foot (7) repositioning to obtain a desired leg (6) and foot (7) vertical alignment for a subsequent footprint digitization.

2. Apparatus (1) according to claim 1 wherein said alignment system of the patient (5) leg (6) with its corresponding foot (7) comprises at least five of said markers (M1-M5), positioned respectively at the internal knee or medial tibial condyle (M1), external knee or lateral tibial condyle (M2), internal malleolus (M3), external malleolus (M4) and foot dorsum or space between the second and third metatarsal (M5).

3. Apparatus (1) according to claim 1 wherein said alignment system of the patient (5) leg (6) with its corresponding foot (7) comprises at least seven of said markers (M1-M7), positioned respectively at the internal knee or medial tibial condyle (M1), external knee or lateral tibial condyle (M2), lateral malleolus (M3), medial malleolus (M4), cuboid bone (M5), *astragalus* or scaphoid bone salience (M6), foot spine or space between the second and third metatarsal (M7).

4. Apparatus (1) according to claim 1, wherein the upper plane of said platform (3) is able to be automatically adjusted so as to be brought into a condition of said tibia verticality, or in a condition in which a line (9) which originates in a middle point of a segment between the lateral tibial condyle and the medial tibial condyle is vertically aligned in the frontal and lateral plane and which passes at a midpoint of a segment between the lateral malleolus and the medial malleolus.

5. Apparatus (1) according to claim 1, wherein at least one of said micrometric adjustment devices (8) is positioned medially in correspondence with one foot (7) side and at least another of said micrometric adjustment devices (8) is placed laterally at the opposite foot (7) side.

6. Apparatus (1) according to claim 1, wherein said micrometric adjustment devices (8) are provided with at least two degrees of freedom, preferably at least three degrees of freedom, still more preferably five degrees of freedom, in order to allow the best possible adjustment based on different feet (7) morphology, wherein said micrometric adjustment devices (8) are selected from: a) lateral sliding to adapt to the foot length (7), b) height adjustment, c) lateral depth adjustment, d) lateral rotation adjustment with respect to the foot (7), and e) lever with pad for support on scaphoid/talus, wherein said lever exerts a rotating pressure to realign a meso-foot.

7. Apparatus (1) according to claim 1, which further comprises a stereo-visual system consisting of a plurality of television cameras (4) positioned frontally with respect to said seating position (2) capable of detecting a space positioning of said markers (M).

8. Apparatus (1) according to claim 1, wherein said central unit is able to analyze in real time the data relating to said leg (6) and foot (7) alignment in the three space planes, and it is able to automatically supply the indications of the numerical and directional movements necessary to automatically bring the platform (3) into precise coordinates required to obtain the correct leg (6) and foot (7) repositioning and vertical alignment for the subsequent footprint (7) digitization.

9. Apparatus (1) according to claim 1, wherein said support platform (3) is constituted by a transparent portion of a laser scanning device, integrated in said platform (3), electronically powered and controlled by said central unit, designed to detect the foot (7) in a neutral position on said support platform (3) in order to be able to carry out the footprint digitization.

10. Method for footprint digitizing a foot (7) of a patient (5) which includes the steps of:

a) placing the patient (5) in a sitting position;

b) allowing the patient (5) to rest the foot (7) on a support platform (3);

c) detecting a correct patient's (5) leg (6) and foot (7) alignment so that the tibia is in a vertical position using at least one marker (M) placed at the knee in front of a middle point of a segment that joins the lateral and medial femoral condyle and at least one other marker (M) located at a space between the second and third metatarsal;

d) positioning the foot (7) in a neutral position by exerting a rotating force on the scaphoid and/or cuboid bones, by means of a lever (10) and at least two micrometric adjustment devices (8), also called turrets (8), placed laterally with respect to the foot (7) and able to slide on a track along a platform (3) direction, wherein at least one of said turrets (8) is able to allow at least one first adjustable pressure pad to be applied into contact of the talus and/or scaphoid inside the foot (7) and at least another of said turrets (8) is able to allow at least one second adjustable pressure pad to be applied into contact with the heel and/or cuboid outside the foot (7), without placing anything under the foot sole;

e) carrying out the continuous numerical data measurement relating to said leg (6) and foot (7) alignment in the three space planes of the foot (7) in the neutral position by means of a stereo-visual system consisting of a plurality of cameras able to detect said markers position;

f) transmitting to a central unit the measured data of said continuous numerical measurement for processing and storing said data to obtain the the footprint (7) digitization;

g) allowing said central unit to possibly provide the indications to correctly repositioning the foot (7) to obtain a desired leg (6) and foot (7) vertical alignment.

* * * * *